US012746085B2

(12) United States Patent
Song et al.

(10) Patent No.: US 12,746,085 B2
(45) Date of Patent: Sep. 29, 2026

(54) MASTER DEVICE FOR VASCULAR INTERVENTION PROCEDURE

(71) Applicant: NAVIGANTIS, INC., Miami, FL (US)

(72) Inventors: Hwa Seob Song, Gyeonggi-do (KR); Hyun Seok Yoon, Gyeonggi-do (KR); Jong Tae Seo, Gyeonggi-do (KR)

(73) Assignee: NAVIGANTIS, INC., Miami, FL (US)

( * ) Notice: Subject to any disclaimer, the term of this patent is extended or adjusted under 35 U.S.C. 154(b) by 0 days.

(21) Appl. No.: 19/306,104

(22) Filed: Aug. 21, 2025

(65) Prior Publication Data

US 2025/0366944 A1 Dec. 4, 2025

Related U.S. Application Data

(63) Continuation of application No. PCT/KR2024/006921, filed on May 22, 2024.

(30) Foreign Application Priority Data

May 25, 2023 (KR) ........................ 10-2023-0067755
May 22, 2024 (KR) ........................ 10-2024-0066496

(51) Int. Cl.
*A61B 34/37* (2016.01)
*A61B 17/00* (2006.01)
(Continued)

(52) U.S. Cl.
CPC ........ *A61B 34/37* (2016.02); *A61B 17/00234* (2013.01); *A61B 17/12* (2013.01);
(Continued)

(58) Field of Classification Search
CPC ......... A61B 34/37; A61B 34/00; A61B 34/20; A61B 34/25; A61B 34/30; A61B 34/35;
(Continued)

(56) References Cited

U.S. PATENT DOCUMENTS

2002/0087169 A1* 7/2002 Brock ................ A61B 17/0469
606/139
2006/0058647 A1* 3/2006 Strommer ............ A61B 5/7475
600/434
(Continued)

FOREIGN PATENT DOCUMENTS

JP 2021-509053 A 3/2021
KR 10-2009-0034813 A 4/2009
(Continued)

OTHER PUBLICATIONS

International Search Report issued Sep. 4, 2024 in International Application No. PCT/KR2024/006921.
(Continued)

*Primary Examiner* — Tasnim Mehjabin Ahmed
(74) *Attorney, Agent, or Firm* — Sughrue Mion, PLLC

(57) ABSTRACT

A vascular interventional procedure master device is provided. The vascular interventional procedure master device may include: an operation rod configured to be manipulated by an operator and perform translational and rotational motions; a rotation unit being configured to operate in conjunction with the rotational motion of the operation rod; a first measurement unit configured to measure a physical quantity related to the translational motion of the operation rod such that a remote control signal to be provided to a slave device is generated based on the translational motion of the operation rod; and a second measurement unit configured to measure a physical quantity related to the rotational motion of the operation rod such that a remote control signal to be provided to the slave device is generated based on the rotational motion of the operation rod.

29 Claims, 15 Drawing Sheets

(51) Int. Cl.

| | |
|---|---|
| ***A61B 17/12*** | (2006.01) |
| ***A61B 17/22*** | (2006.01) |
| ***A61B 34/00*** | (2016.01) |
| ***A61B 34/20*** | (2016.01) |
| ***A61B 34/30*** | (2016.01) |
| ***A61B 34/35*** | (2016.01) |
| ***A61B 90/00*** | (2016.01) |
| ***A61F 2/95*** | (2013.01) |
| ***A61M 25/01*** | (2006.01) |

(52) U.S. Cl.
CPC .............. *A61B 17/22* (2013.01); *A61B 34/00* (2016.02); *A61B 34/20* (2016.02); *A61B 34/25* (2016.02); *A61B 34/30* (2016.02); *A61B 34/35* (2016.02); *A61B 90/00* (2016.02); *A61F 2/95* (2013.01); *A61M 25/01* (2013.01); *A61B 2017/00292* (2013.01); *A61B 2034/2074* (2016.02); *A61B 2034/254* (2016.02); *A61B 2034/301* (2016.02)

(58) Field of Classification Search
CPC . A61B 34/301; A61B 17/00234; A61B 17/12; A61B 17/22; A61B 90/00; A61B 2017/00292; A61B 2034/2074; A61B 2034/254; A61B 2034/301; A61M 25/01
See application file for complete search history.

(56) References Cited

U.S. PATENT DOCUMENTS

| | | | | |
|---|---|---|---|---|
| 2008/0004603 | A1 | 1/2008 | Larkin et al. | |
| 2017/0209232 | A1 | 7/2017 | Larkin et al. | |
| 2017/0210012 | A1 | 7/2017 | Larkin et al. | |
| 2017/0305016 | A1 | 10/2017 | Larkin et al. | |
| 2018/0056044 | A1* | 3/2018 | Choi ...................... | A61B 34/30 |
| 2018/0297206 | A1 | 10/2018 | Larkin et al. | |
| 2019/0125385 | A1 | 5/2019 | Scheib et al. | |
| 2019/0192247 | A1 | 6/2019 | Woo et al. | |
| 2019/0201158 | A1 | 7/2019 | Shelton, IV et al. | |
| 2020/0331147 | A1 | 10/2020 | Larkin et al. | |
| 2020/0367977 | A1* | 11/2020 | Liu ........................ | A61B 34/30 |
| 2023/0107307 | A1 | 4/2023 | Liu et al. | |
| 2024/0000532 | A1 | 1/2024 | McGrogan et al. | |
| 2024/0341871 | A1 | 10/2024 | Liu et al. | |

FOREIGN PATENT DOCUMENTS

| | | | |
|---|---|---|---|
| KR | 10-2017-0132101 | A | 12/2017 |
| KR | 10-2018-0042762 | A | 4/2018 |
| KR | 10-2020-0109056 | A | 9/2020 |
| KR | 10-2022-0012286 | A | 2/2022 |
| KR | 10-2365859 | B1 | 2/2022 |
| WO | 2023/029582 | A1 | 3/2023 |

OTHER PUBLICATIONS

Communication dated Jan. 22, 2026 in Korean Application No. 10-2024-0066496.

* cited by examiner

Leader and follower mode

Tip sync motion mode

Vibration mode

Back-and-return mode

Back-and-return mode

MASTER DEVICE FOR VASCULAR INTERVENTION PROCEDURE

CROSS-REFERENCE TO RELATED APPLICATION

This application is a Bypass Continuation Application of PCT International Application No. PCT/KR2024/006921, filed on May 22, 2024 and designating the United States, the international application being based upon and claiming the benefit of priority from Korean Patent Application No. 10-2023-0067755, filed on May 25, 2023, and Korean Patent Application No. 10-2024-0066496, filed on May 22, 2024, the entire contents of which are hereby incorporated by reference.

TECHNICAL FIELD

Some embodiments of this present disclosure relate to, for example, a vascular interventional procedure master device.

BACKGROUND

A vascular interventional procedure is a minimally invasive procedure used to treat vascular diseases or cancer, and is mainly performed under X-ray fluoroscopy, during which a thin catheter with a diameter of several millimeters or less is percutaneously inserted through a blood vessel to a lesion site, thereby reaching a target organ for treatment. Currently, representative vascular interventional procedures performed in South Korea and around the world include trans-arterial chemoembolization (TACE) for liver cancer, percutaneous vascular angioplasty, and artificial blood vessel stent placement for aortic diseases.

Blood vessels mostly branch into multiple branches or are formed in a curved shape. Therefore, in a vascular interventional procedure, introducers having multiple diameters, known as a coaxial system of a catheter and a guidewire, are overlapped and used to prevent vascular damage. Additionally, in a vascular interventional procedure, a vascular interventional procedure master-slave system, which enables remote control of procedure tools, is used to reduce an operator's radiation exposure.

When inserting the procedure tool up to a target branch while controlling the procedure tool, consecutively encountering challenging regions such as narrowed or curved segments due to disease may cause delays in the procedure tool insertion.

Therefore, there may be a need for a solution that enables precise remote control of a procedure tool's operation to prevent delays in insertion of the procedural instrument.

SUMMARY

One of the technical problems to be solved by the present disclosure is to provide a vascular interventional procedure master device that enables precise remote control of the operation of a procedure tool through various operation modes so that the procedure tool can be smoothly inserted up to a target branch.

Technical problems to be solved by the present disclosure are not limited to the above-described technical problem.

The present disclosure may provide a vascular interventional procedure master device.

According to an embodiment, the vascular interventional procedure master device may include: an operation rod configured to be manipulated by an operator and perform translational and rotational motions; a rotation unit into which a longitudinal front end side of the operation rod is inserted, a guide hole being formed in the rotation unit in a longitudinal direction to guide the translational motion of the inserted operation rod, and the rotation unit being configured to operate in conjunction with the rotational motion of the operation rod; a first measurement unit connected to one longitudinal side of the operation rod exposed outside the rotation unit, and configured to, in case that the operation rod performs a translational motion, measure a physical quantity related to the translational motion of the operation rod such that a remote control signal to be provided to a slave device, configured to drive a procedure tool inserted into a body, is generated based on the translational motion of the operation rod; and a second measurement unit connected to the rotating unit and configured to, in case that the operation rod performs a rotational motion, measure a physical quantity related to the rotational motion of the operation rod such that a remote control signal to be provided to the slave device is generated based on the rotational motion of the operation rod.

According to an embodiment, the master device may further include a housing, wherein the housing includes: a housing body having an inner space; and a partition wall provided in the inner space of the housing body to divide the inner space into a first space and a second space. The rotation unit may be installed in the first space in a horizontal direction, and both longitudinal ends of the rotation unit are bearing-coupled to opposite walls of the first space. The longitudinal front end side of the operation rod may pass through the second space from outside the second space and be inserted into the rotation unit installed in the first space, and a longitudinal rear end may protrude outward from the second space so as to be grasped by the operator.

According to an embodiment, the first measurement unit may be disposed in the second space and axially coupled to the operation rod located in the second space, and the second measurement unit may be disposed in the first space and gear-coupled to the rotation unit.

According to an embodiment, the master device may further include a display unit, wherein the display unit is configured to output a user interface related to the procedure tool so as to allow the operator to make a selection.

According to an embodiment, the master device may further include a control unit, wherein the control unit is configured to, in case that a leader and follower mode provided on the user interface is selected, configure any one procedure tool, which is controlled based on a remote control signal generated based on the motion of the operation rod, as a leader and configure at least one other procedure tool, which is not remotely controlled, as a follower, and generate a remote control signal for operating the follower such that the follower follows an operation of the leader, and provide the remote control signal to the slave device.

According to an embodiment, the master device may further include a control unit, wherein the control unit is configured to, in case that a tip sync motion mode provided on the user interface is further selected, generate a remote control signal for operating the follower such that a distance between the tip of the leader and the tip of the follower becomes zero, and provide the remote control signal to the slave device.

According to an embodiment, the master device may further include a control unit, wherein the control unit is configured to, in case that a screw motion mode provided on the user interface is selected, control the operation rod such that the translational motion and rotational motion of the operation rod are performed simultaneously.

According to an embodiment, the master device may further include a control unit, wherein the control unit is configured to, in case that a vibration mode provided on the user interface is selected, generate a remote control signal for generating a vibration such that when a procedure tool, controlled by the remote control signal generated based on the motion of the operation rod is operated, the vibration is applied to the procedure tool, and provide the remote control signal to the slave device.

According to an embodiment, the master device may further include a control unit, wherein the control unit is configure to: analyze a sensing value transmitted from a position sensor installed in each of multiple modules supporting respective procedure tools in the slave device such that collisions between the multiple modules are avoid in case that each of the multiple modules advances, retracts, or stops; and generate, based on the analyzed sensing value, a remote control signal that reconfigures a movement operation of each of the multiple modules, and provide the remote control signal to the slave device. The control unit may be configured to output, on the display unit, an alarm regarding the reconfigured movement operation of each of the multiple modules such that the operator is able to identify the alarm.

According to an embodiment, when a drug is injected through the procedure tool, a back-and-return mode provided on the user interface is selected. The master device may further include a control unit, wherein the control unit is configured to: in case that the back-and-return mode is selected, generate a remote control signal for retracting another procedure tool, which is inserted into one procedure tool, such that the other procedure tool is completely withdrawn from the inside to the outside of the procedure tool, and provide the remote control signal to the slave device; and in case that drug injection using the one procedure tool is completed, generate a remote control signal for advancing the other procedure tool such that the other procedure tool is reinserted into the original position inside the one procedure tool, and provide the remote control signal to the slave device.

According to an embodiment, the master device may further include a control unit, wherein the control unit is configured to, in case that an anti-stent jumping motion mode provided on the user interface is selected, generate, before placing a stent within a blood vessel, a remote control signal for retracting the stent such that when a procedure tool, which is controlled by a remote control signal generated based on the motion of the operation rod, the stent is also retracted, and to provide the remote control signal to the slave device, wherein a distance by which the stent is retracted may be shorter than a distance by which the procedure tool is retracted.

According to an embodiment, the master device may further include a control unit, wherein the control unit is configured to generate an alarm recognizable to the operator whenever a procedure tool, which is controlled based on a remote control signal generated based on the motion of the operation rod by the operator's manipulation, performs a translational motion of a predetermined distance.

According to an embodiment, the master device may further include a control unit, wherein the control unit is configured to, in case that a procedure tool, controlled by a remote control signal generated based on the motion of the operation rod by the operator's manipulation, is operated, and that a position of another procedure tool interacting with the procedure tool is moved by the operation of the procedure tool, generate a remote control signal for operating the other procedure tool such that position compensation is performed to return the other procedure tool to an original position, and provide the remote control signal to the slave device.

According to an embodiment, the master device may further include a control unit, wherein the control unit is configured to automatically return the operation rod to an initial position in case that a stroke higher than a predetermined stroke is applied to the operation rod for the translational motion and rotational motion of the operation rod.

According to an embodiment, the vascular interventional procedure master device may include: an operation rod configured to be manipulated by an operator and capable of a translational motion and a rotational motion; a rotation unit into which a longitudinal front end side of the operation rod is inserted, a guide hole being formed in the rotation unit in a longitudinal direction to guide the translational motion of the inserted operation rod, and the rotation unit being configured to operate in conjunction with the rotational motion of the operation rod; a first measurement unit connected to one longitudinal side of the operation rod exposed outside the rotation unit, and configured to, in case that the operation rod performs a translational motion, measure a physical quantity related to the translational motion of the operation rod such that a remote control signal to be provided to a slave device, configured to drive a procedure tool inserted into a body, is generated based on the translational motion of the operation rod; and a second measurement unit connected to the rotating unit and configured to, in case that the operation rod performs a rotational motion, measure a physical quantity related to the rotational motion of the operation rod such that a remote control signal to be provided to the slave device is generated based on the rotational motion of the operation rod.

Accordingly, the vascular interventional procedure master device may be provided, which is capable of performing precise remote control of the operation of a procedure tool such that the procedure tool can be smoothly inserted up to a target branch.

In other words, according to the embodiment of the present disclosure, operation modes related to the motion of a procedure tool, such as screw motion mode, leader and follower mode, tip sync motion mode, vibration mode, back-and-return mode, and anti-stent jumping motion mode, among others, are provided on a user interface so as to be selectable by an operator. As a result, even when encountering challenging regions such as regions narrowed due to disease, the procedure tool can easily and smoothly pass through the challenging regions, thereby enhancing the efficiency of the vascular interventional procedure.

DETAILED DESCRIPTION

Figure 1:
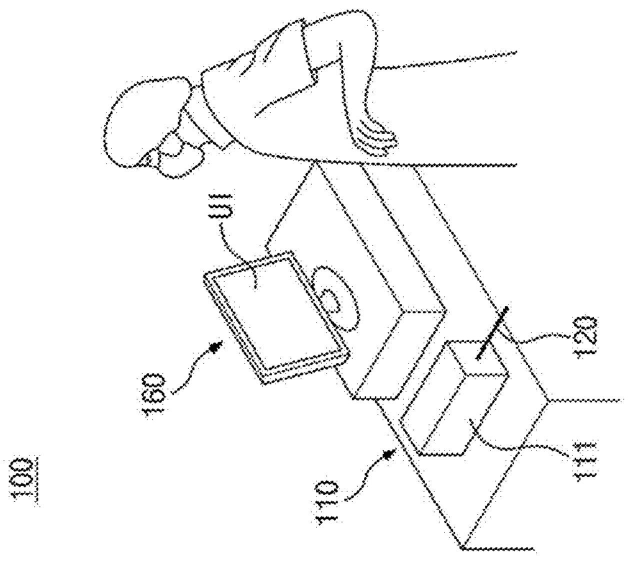
FIG. 1 illustrates a vascular interventional system including a vascular interventional procedure master device and a slave device according to an embodiment of the present disclosure.
Figure 1:
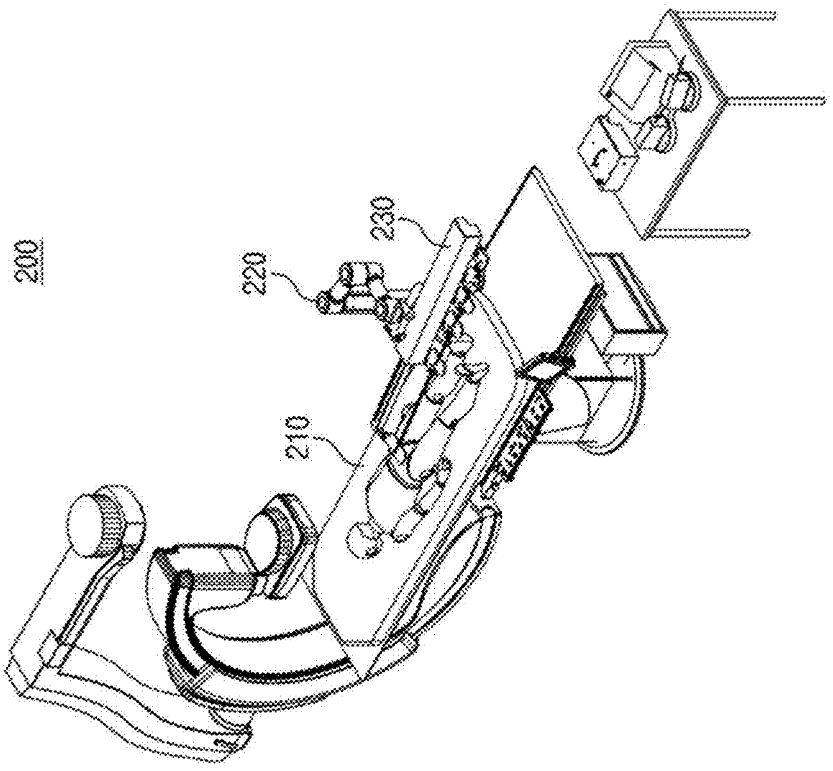

Hereinafter, embodiments of the present disclosure will be described in detail with reference to the accompanying drawings. However, the technical idea of the present disclosure is not limited to the embodiments described herein and may be embodied in other forms. Rather, the embodiments described herein are provided to ensure that the disclosure may be thorough and complete, and that the idea of the present disclosure may be fully conveyed to those skilled in the art.

In the present specification, when a component is referred to as being on another component, this means that the component may be formed directly on the other component or that a third component may be interposed therebetween. In addition, in the drawings, shapes and sizes are exaggerated for effective illustration of the technical content.

Further, terms such as "first," "second," and "third" are used in various embodiments of the present specification to describe various components, but these components should not be limited by such terms. These terms are merely used to distinguish one component from another. Therefore, a component referred to as a first component in an embodiment may be referred to as a second component in another embodiment. Each embodiment described and exemplified herein also includes complementary embodiments thereof. In addition, the term "and/or" in the present specification is used to mean including at least one of components listed before or after the term.

In the specification, singular expressions include plural expressions unless the context clearly indicates otherwise. In addition, the terms "include" or "have" are intended to designate the presence of the features, numbers, steps, components, or combinations thereof described in the specification and should not be construed to exclude the possibility of the presence or addition of one or more other features, numbers, steps, components, or combinations thereof. Further, in the specification, the term "connecting" is used to encompass both indirectly connecting and directly connecting multiple components.

In addition, terms such as " . . . unit," " . . . device," and "module" as used in the specification refer to a unit configured to perform at least one function or operation, and may be implemented by hardware, software, or a combination of hardware and software.

Further, in describing the present disclosure below, detailed descriptions of related known functions or configurations will be omitted when such detailed descriptions are deemed to unnecessarily obscure the subject matter of the present disclosure.

FIGS. 1 to 28 illustrate a vascular interventional procedure master device according to an embodiment of the present disclosure.

As illustrated in FIG. 1, a vascular interventional procedure master device 100 according to an embodiment of the present disclosure may constitute a vascular interventional procedure system with a slave device 200.

In the vascular interventional procedure system, an operator may remotely control the slave device 200 via the master device 100, and thus remote procedures may be performed via the slave device 200. With such a vascular interventional procedure system, radiation exposure of the operator may be minimized.

The slave device 200 remotely controlled by the vascular interventional procedure master device 100 according to an embodiment of the present disclosure may include a bed 210, a frame 220, and a vascular interventional procedure robot 230.

The bed 210 may provide a procedure surface on which a patient may lie to undergo a procedure while lying down. In this case, the frame 220 may be movably installed on the bed 210. The frame 220 may support the vascular interventional procedure robot 230.

The vascular interventional procedure robot 230 may be mounted to the frame 220. In this case, the vascular interventional procedure robot 230 may be mounted to be able to perform rotational or translational motions with respect to the frame 220.

The vascular interventional procedure robot 230 may rotate a procedure tool (10 in FIG. 5) in a roll direction or translate the procedure tool forward or backward, in order to insert the procedure tool (10 in FIG. 5) into the body and move the procedure tool to a target branch. Further, the vascular interventional procedure robot 230 may rotate and simultaneously translate the procedure tool (10 in FIG. 5).

The operator may remotely control the vascular interventional procedure robot 230 via the vascular interventional master device 100, while inserting the procedure tool (10 in FIG. 5) operated by the vascular interventional procedure robot 230 up to the target branch.

Figure 13:
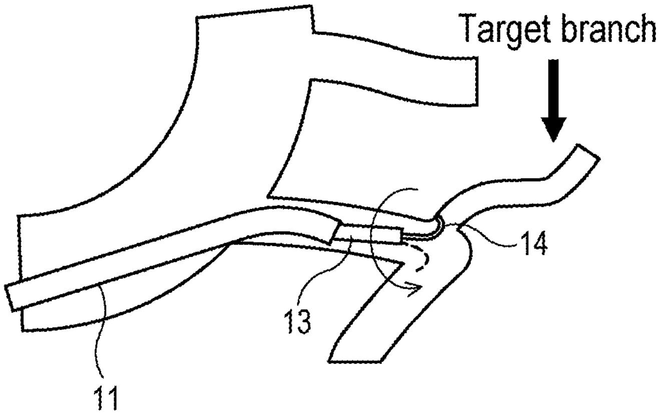

Here, the procedure tool (10 in FIG. 5) may be one of a catheter (11 in FIG. 5) that is inserted into the body, a guidewire (or guide device) (12 in FIG. 5) that is inserted into the catheter (11 in FIG. 5), a microcatheter (13 in FIG. 13) that is inserted into the catheter (11 in FIG. 5), and a micro guidewire (14 in FIG. 13) that is inserted into the microcatheter (13 in FIG. 13). At least one procedure device may include a microcatheter (13 in FIG. 13).

The vascular interventional procedure master device 100, according to an embodiment of the present disclosure, may remotely operate the procedure tool (10 in FIG. 5) by providing a remote control signal generated by the operator to the vascular interventional procedure robot 230 of the slave device 200.

Figure 2:
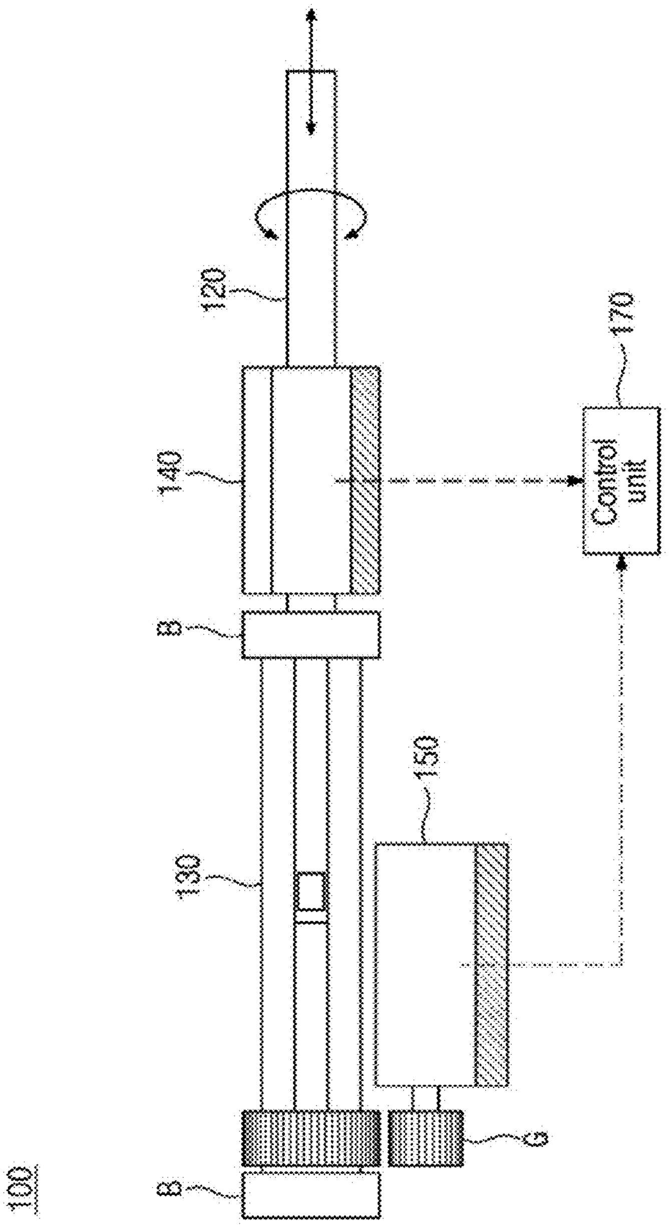
FIGS. 2 and 3 illustrate a vascular interventional procedure master device according to an embodiment of the present disclosure.
Figure 3:
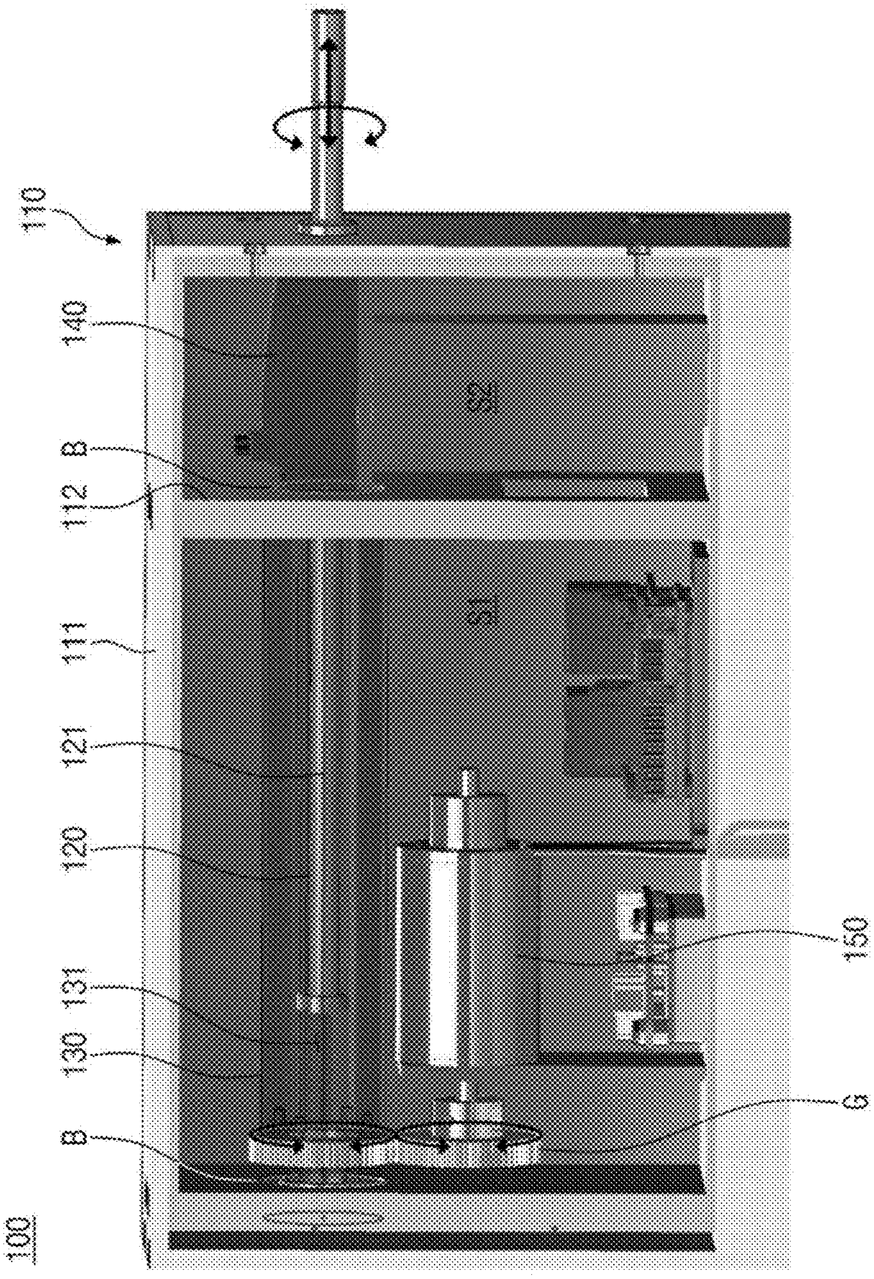
Figure 5:
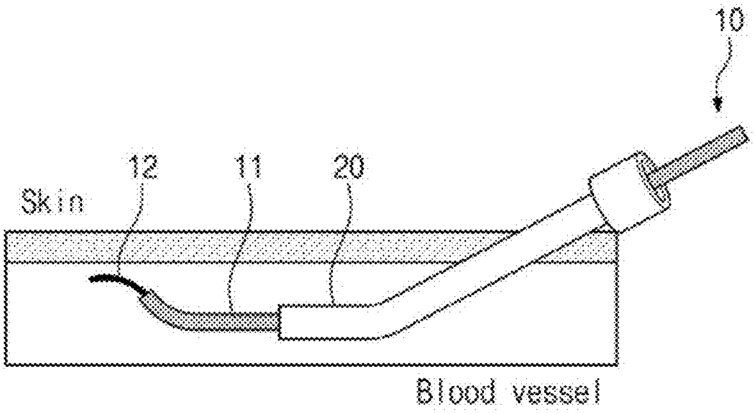

Referring to FIGS. 2 and 3, the vascular interventional procedure master device 100 according to an embodiment of the present disclosure may include an operation rod 120, a rotation unit 130, a first measurement unit 140, and a second measurement unit 150 in order to generate remote control signals regarding the operation of the procedure tool (10 in FIG. 5).

In this case, the vascular interventional procedure master device 100 according to an embodiment of the present disclosure may further include a housing 110.

The housing 110 may provide an installation space for the operation rod 120, the rotation unit 130, the first measurement unit 140, and the second measurement unit 150. By being installed in the housing 110, the operation rod 120, the rotation unit 130, the first measurement unit 140, and the second measurement unit 150 may be modularized.

According to an embodiment of the present disclosure, the housing 110 may include a housing body 111 and a partition wall 112.

The housing body 111 forms an exterior of the housing 110. The housing body 111 may be provided in the form of a hexahedron extending in one direction.

In this case, the housing body 111 may have an inner space. The operation rod 120, the rotation unit 130, the first measurement unit 140, and the second measurement unit 150 may be disposed in the inner space.

On a wall surface at one longitudinal end of the housing body 111, a mounting hole may be provided in which a bearing B coupled to one longitudinal end of the rotation unit 130 is mounted. An insertion hole may be provided on a wall surface at the other longitudinal end of the housing body so that the operation rod 120 can be horizontally inserted from the outside to the inside of the housing body 111.

The partition wall 112 may be arranged in the inner space of the housing body 111. The partition wall 112 may be arranged in a vertical direction on one side of the inner space of the housing body 111.

Accordingly, the inner space of the housing body 111 may be divided into a first space S1 and a second space S2. In this case, the partition wall 112 may be installed in the vertical direction on one side of the inner space of the housing body 111 such that the first space S1 is wider than the second space S2.

Meanwhile, a through-hole may be provided in one side of the partition wall 112. The operation rod 120 may longitudinally pass through the through-hole, and the bearing B coupled to the other longitudinal end of the rotation unit 130 may be disposed in the through-hole.

The operation rod 120 may be provided in the form of a cylindrical bar extending in one direction. The operation rod 120 may be arranged to perform translational and rolling motions in response to manipulation of the operator.

For ease of manipulation by the operator, the operation rod 120 may have a diameter that allows the operator to easily control the operation rod while grasping the operation rod with the fingers.

According to an embodiment of the present disclosure, the operation rod 120 may be inserted into the housing body 111 through the insertion hole provided in the wall surface at the other longitudinal end of the housing body 111.

Specifically, the operation rod 120 may be inserted into the first space S1 while passing through the second space S2 from the outside of the second space S2. In this case, the longitudinal front end of the operation rod 120 inserted into the first space S1 may be inserted into the rotation unit 130 installed in the first space S1.

As described above, the operation rod 120 may be configured to be manipulated by the operator. To this end, the longitudinal rear end of the operation rod 120, which has the longitudinal front end inserted into the first space S1, may protrude outward from the second space S2 so as to be grasped by the operator. Thus, the longitudinal rear end of the operation rod 120 that protrudes outward from the second space S2 may act as a handle or a manipulation lever that is grasped by the operator.

Accordingly, while grasping the longitudinal rear end of the operation rod 120 that protrudes outward from the second space S2 with the fingers, the operator may advance the operation rod 120 by pushing the operation rod 120 into the housing body 111 or retract the operation rod 120 by pulling the operation rod 120 outward from the housing body 111.

Additionally, the operator may roll the operation rod 120 while grasping the longitudinal rear end of the operation rod 120, which protrudes outward from the second space S2, with the fingers.

In this case, according to an embodiment of the present disclosure, the operator may rotate the operation rod 120 while advancing or retracting the operation rod 120, thereby allowing the remotely controlled procedure tool (10 in FIG. 5) to easily pass through the curved portions of a blood vessel. This will be described in more detail below.

According to an embodiment of the present disclosure, the operation rod 120 may be translated and rotated by manipulation of the operator, and based on the translational and rotational motions of the operation rod, a remote control signal may be generated that is provided to the vascular interventional procedure robot 230 of the slave device 200 that drives the procedure tool (10 in FIG. 5).

To generate the remote control signal, the operation rod 120 may be connected to the first measurement unit 140 for measuring the physical quantity of translational motion and the second measurement unit 150 for measuring the physical quantity of rotational motion.

Figure 4:
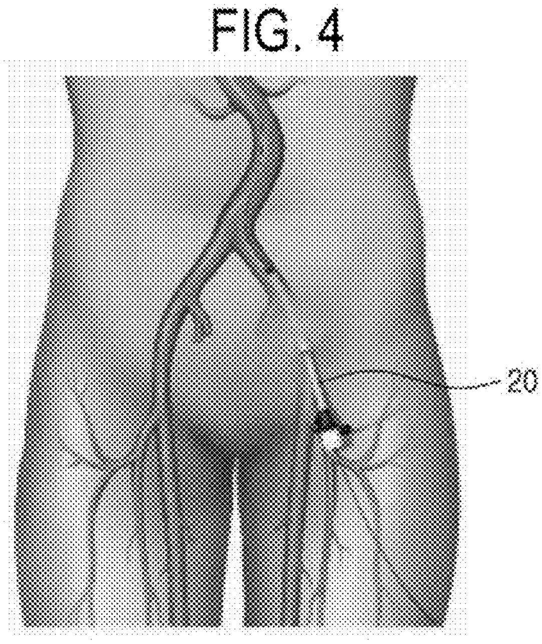
FIGS. 4 to 17 illustrate a process of a vascular intervention procedure using procedure tools that are remotely controlled by a vascular interventional procedure master device according to an embodiment of the present disclosure.

As illustrated in FIG. 4, for a vascular interventional procedure, a vascular puncture is first made, and an introducer sheath 20 may be inserted into the punctured site.

Then, as illustrated in FIG. 5, the procedure tool 10, the catheter 11 and the guidewire 12 that is inserted into the catheter 11, may be inserted into a blood vessel via the introducer sheath 20.

Figure 6:
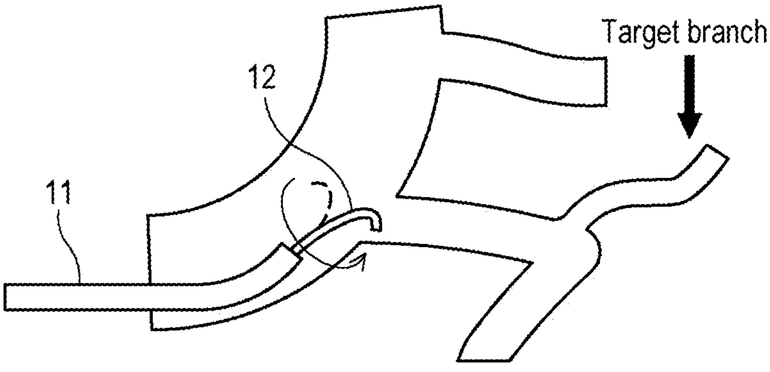
Figure 7:
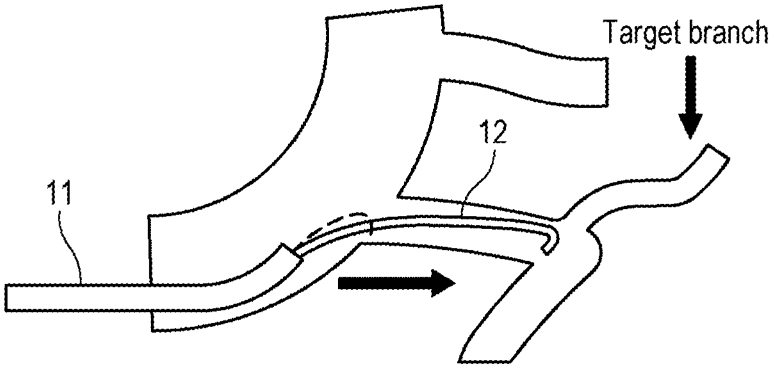

Then, as illustrated in FIGS. 6 and 7, in order to cause the guidewire 12 to reach a target branch, the operator may manipulate the operation rod 120, for example, so that the operation rod 120 rolls and advances in the clockwise direction.

Accordingly, a remote control signal generated based on the motion of the operation rod 120 may be provided to the vascular interventional procedure robot 230 and the guidewire 12 may be rotated and inserted toward the target branch by the vascular interventional procedure robot 230.

Figure 8:
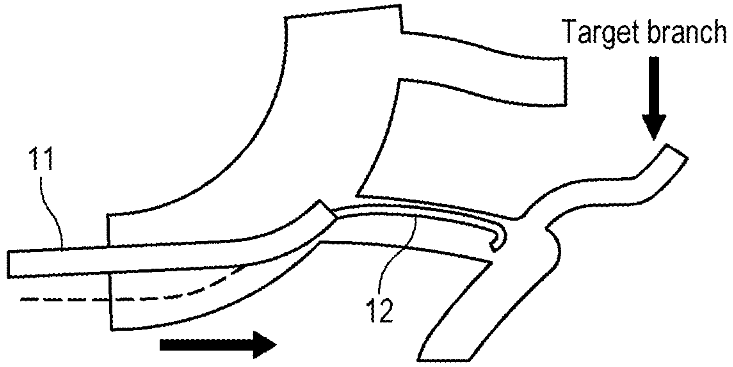
Figure 9:
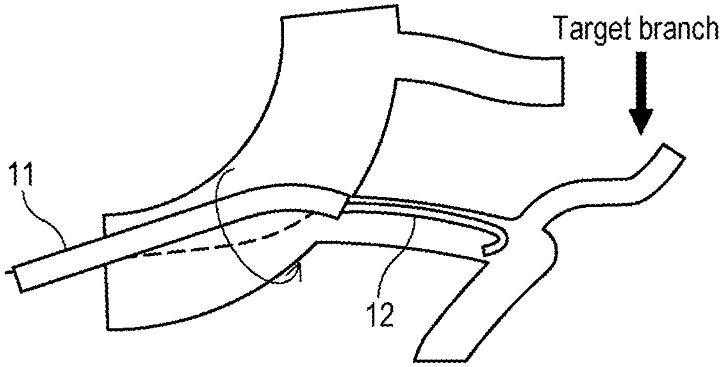
Figure 10:
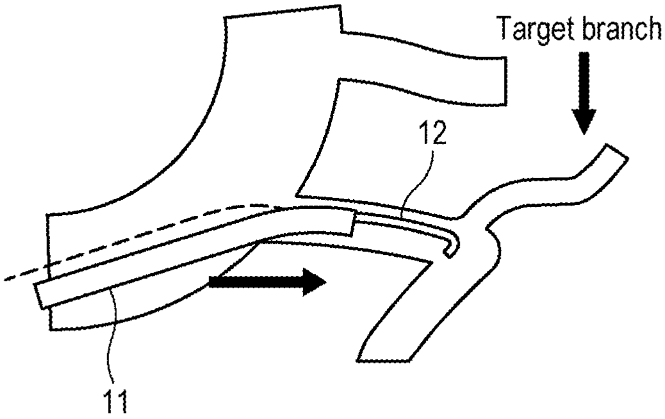

Then, as illustrated in FIGS. 8 to 10, to advance the catheter 11 to the target branch along the guidewire 12, the operator may manipulate the operation rod 120 such that the operation rod 120 is advanced, rotated, and advanced.

Accordingly, a remote control signal generated based on the motion of the operation rod 120 may be provided to the vascular interventional procedure robot 230, and the catheter 11 may be inserted along the guidewire 12 while being rotated by the vascular interventional procedure robot 230.

Here, the procedure tool 10 may be selected via a user interface (UI) described below. That is, the operator may replace the remotely controlled procedure tool 10 according to the surgical procedure through the user interface (UI).

Figure 11:
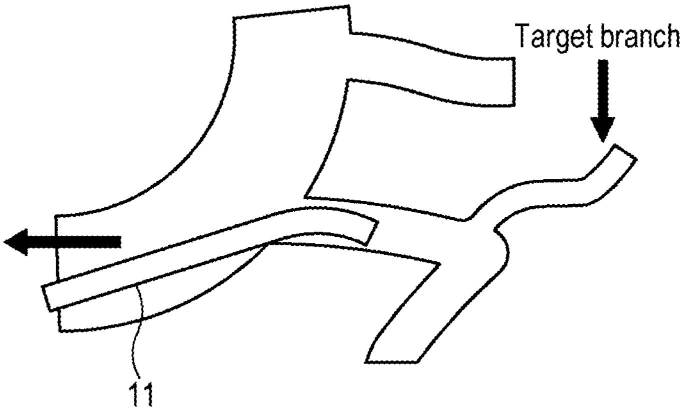

Then, as illustrated in FIG. 11, the operator may manipulate the operation rod 120 such that the operation rod 120 is retracted.

Accordingly, a remote control signal generated based on the motion of the operation rod 120 may be provided to the vascular interventional procedure robot 230, and the guidewire 12 may be removed from the catheter 11 while being withdrawn in a direction opposite to that of insertion by the vascular interventional procedure robot 230.

Figure 12:
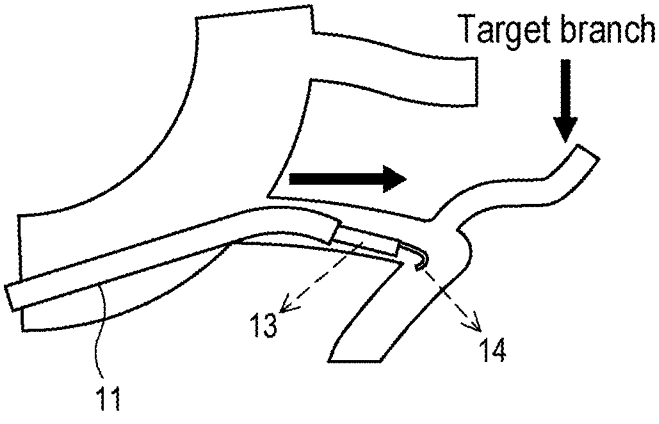

Then, as illustrated in FIG. 12, the operator may manipulate the operation rod 120 such that the operation rod 120 is advanced.

Accordingly, a remote control signal generated based on the motion of the operation rod 120 may be provided to the vascular interventional procedure robot 230, and the microcatheter 13 inserted into the catheter 11 and the micro guidewire 14 inserted into the microcatheter 13 may be inserted into the blood vessel by the vascular interventional procedure robot 230.

Figure 14:
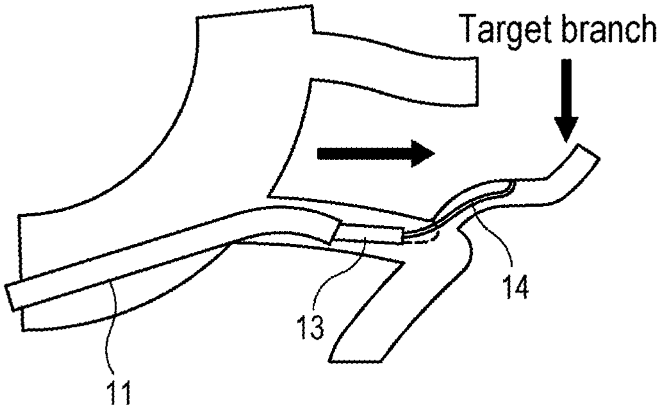

Then, as illustrated in FIGS. 13 and 14, in order to insert the micro guidewire 14 into the target branch, the operator may, for example, manipulate the operation rod 120 such that the operation rod 120 rolls counterclockwise and advances.

Accordingly, a remote control signal generated based on the motion of the operation rod 120 may be provided to the vascular interventional procedure robot 230, and the micro guidewire 14 may be rotated and inserted into the target branch by the vascular interventional procedure robot 230.

Figure 15:
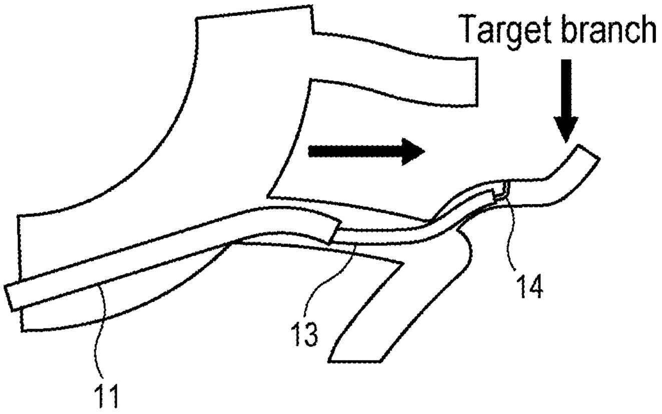

Then, as illustrated in FIG. 15, to insert the microcatheter 13 into the target branch along the micro guidewire 14, the operator may manipulate the operation rod 120 such that the operation rod 120 rolls counterclockwise and advances.

Accordingly, a remote control signal generated based on the motion of the operation rod 120 may be provided to the vascular interventional procedure robot 230, and the microcatheter 13 may be inserted along the micro guidewire 14 while being rotated by the vascular interventional procedure robot 230.

Figure 16:
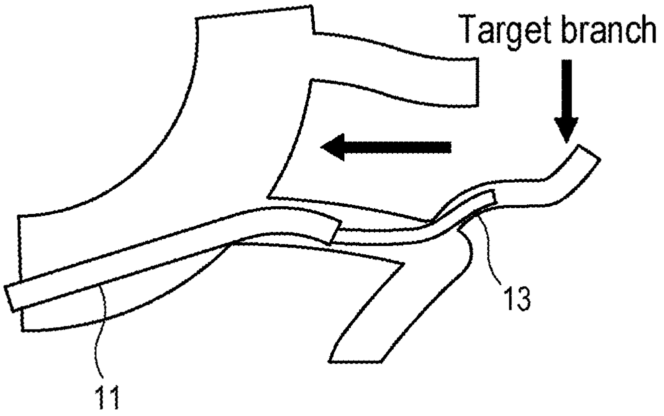

Then, as illustrated in FIG. 16, the operator may manipulate the operation rod 120 such that the operation rod 120 is retracted.

Accordingly, a remote control signal generated based on the motion of the operation rod 120 may be provided to the vascular interventional procedure robot 230, and the micro guidewire 14 may be removed from the microcatheter 13 while being withdrawn in a direction opposite to that of insertion by the vascular interventional procedure robot 230.

Figure 17:
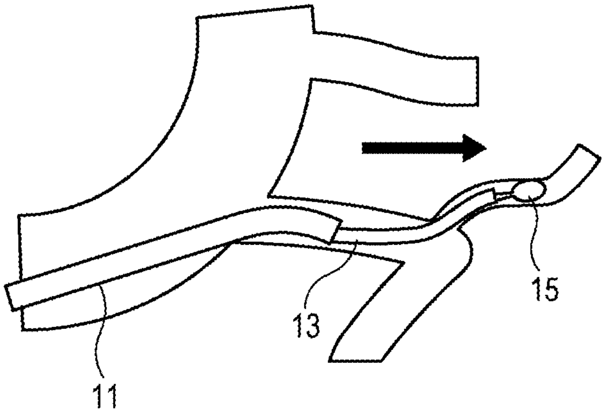

Then, as illustrated in FIG. 17, the operator may manipulate the operation rod 120 to advance the operation rod 120.

Accordingly, a remote control signal generated based on the motion of the operation rod 120 may be provided to the vascular interventional procedure robot 230, and a medical device 15 may be delivered to the target branch through the microcatheter 13 by the vascular interventional procedure robot 230. In addition to the medical device 15, a contrast agent, a drug, an embolic material, and the like may be delivered into the target branch through the microcatheter 13.

Referring again to FIGS. 2 and 3, the rotation unit 130 may be longitudinally connected to the operation rod 120. According to an embodiment of the present disclosure, the longitudinal front end side of the operation rod 120 may be inserted into the rotation unit 130 in the longitudinal direction.

In this case, the rotation unit 130 may include a guide hole 131. The guide hole 131 may be longitudinally arranged in the rotation unit 130.

The guide hole 131 may guide the translational motion, i.e., advancement or retraction, of the operation rod 120 inserted into the rotation unit 130.

According to an embodiment of the present disclosure, the rotation unit 130 may be linked to the rotational motion of the operation rod 120 that is inserted therein. To this end, a trench-shaped concave portion may be formed in the guide hole 131 in the longitudinal direction.

A convex portion formed longitudinally on the operation rod 120 may be seated in the concave portion. Accordingly, during translational motion of the operation rod 120, the rotation unit 130 may only guide an advancement or retraction path and may not be linked to the translational motion of the operation rod 120.

On the other hand, when the operation rod 120 rotates in the roll direction, the rotation unit 130 may also be linked to and rotated in the same direction as the rotation of the operation rod 120. The physical quantity of the rotational motion of the rotation unit 130 may be measured by the second measurement unit 150, and based on this physical quantity, a remote control signal may be generated to rotate the procedure tool 10 in the same direction as the rotation direction of the operation rod 120.

According to an embodiment of the present disclosure, the rotation unit 130 may be horizontally installed in a first space S1 defined inside the housing body 111.

In this case, a bearing B mounted in a mounting hole provided on a wall surface at one longitudinal end of the housing body 111 may be axially coupled to one longitudinal end of the rotation unit 130. Further, a bearing B mounted in a through-hole provided in the partition wall 112 may be axially coupled to the other longitudinal end of the rotation unit 130.

As such, the rotation unit 130 may be bearing-coupled, at both longitudinal ends thereof, to two wall surfaces of the first space S1, respectively. Accordingly, the rotation unit 130 may be linked to the roll-direction rotation of the operation rod 120 and may be rotated in the first space S1 in the roll direction.

The first measurement unit 140 may be connected to one longitudinal side of the operation rod 120, which is exposed outside the rotation unit 130. According to an embodiment of the present disclosure, the first measurement unit 140 may be disposed in a second space S2 defined inside the housing body 111 and may be axially coupled to the operation rod 120 positioned in the second space S2.

The first measurement unit 140 may measure a physical quantity of the translational motion of the operation rod 120 when the operation rod 120 is moved translationally by the operation rod 120.

For example, the first measurement unit 140 may measure a translational velocity, a translational distance, and a translational direction of the operation rod 120 when the operation rod 120 is moved translationally by an operator.

A remote control signal provided to the slave device 200, more specifically, to the vascular interventional procedure robot 230 for driving the procedure tool 10 inserted into the body, may be generated based on the physical quantity of translational motion of the operation rod 120 as measured by the first measurement unit 140.

Accordingly, the remote control signal based on the translational motion of the operation rod 120 may be provided to the vascular interventional procedure robot 230, and thus, the physical quantity of the translational motion of the operation rod 120 may be reflected in the translational motion of the procedure tool 10 driven by the vascular interventional procedure robot 230.

According to an embodiment of the present disclosure, the first measurement unit 140 may be arranged as a combination of a linear motor and a hall sensor.

The linear motor may enable translational motion of the operation rod 120 at the time of manipulation by an operator. Further, the Hall sensor may detect a change in a magnetic field of the linear motor caused by the translational motion of the operation rod 120.

However, this is merely one example, and the first measurement unit 140 is not necessarily limited to a combination of a linear motor and a Hall sensor in the present disclosure.

The second measurement unit 150 may be disposed in the first space S1 defined inside the housing body 111. The second measurement unit 150 may be connected to the rotation unit 130 disposed in the first space S1. According to an embodiment of the present disclosure, the second measurement unit 150 may be gear-coupled to the rotation unit 130. That is, the second measurement unit 150 may be connected to the rotation unit 130 via gears G that intermesh and rotate.

The second measurement unit 150 may measure a physical quantity of the rotational motion of the operation rod 120 when the operation rod 120 is rotated by the operator's manipulation.

For example, when the operation rod 120 is rotated by the operator's manipulation, the second measurement unit 150 may measure a rotation speed, a rotation distance, and a rotation direction of the operation rod 120.

A remote control signal provided to the vascular interventional procedure robot 230 of the slave device 200 may be generated based on the physical quantity of the rotational motion of the operation rod 120, measured by the second measurement unit 150.

Accordingly, a remote control signal based on the rotational motion of the operation rod 120 may be provided to the vascular interventional procedure robot 230, and the physical quantity of the rotational motion of the operation rod 120 may be reflected in the rotational motion of the procedure tool 10 driven by the vascular interventional procedure robot 230.

According to an embodiment of the present disclosure, the second measurement unit 150 may be arranged as a combination of a rotary motor and a Hall sensor.

The rotary motor may be driven according to the rotation of the rotation unit 130, which is linked to the rotation of the operation rod 120. Further, the Hall sensor may detect a change in a magnetic field of the rotary motor caused by the rotation of the rotation unit 130.

However, this is merely one example, and the second measurement unit 150 is not necessarily limited to a combination of a rotary motor and a Hall sensor in the present disclosure.

Referring again to FIG. 1, the vascular interventional procedure master device 100 according to an embodiment of the present disclosure may further include a display unit 160.

The display unit 160 may be provided, for selection by the operator, as a touch screen that displays a user interface (UI) related to the procedure tool 10.

Figure 18:
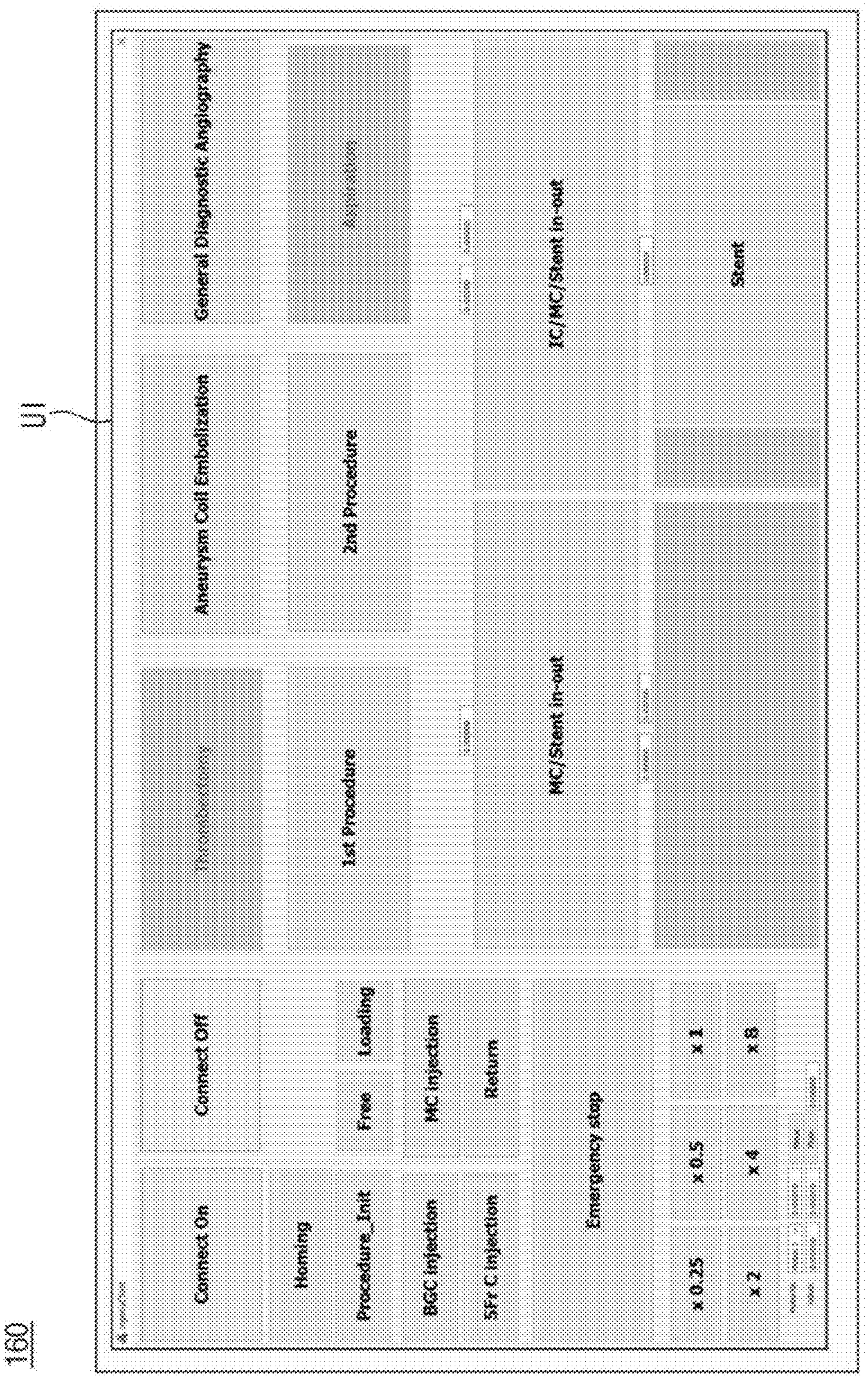
FIG. 18 illustrates a display unit of a vascular interventional procedure master device according to an embodiment of the present disclosure.

As illustrated in FIG. 18, various procedure tool 10 and surgical procedures to be remotely controlled may be provided in the user interface (UI). Accordingly, the operator may select, from the user interface (UI), a remotely controllable procedure tool 10 based on the surgical procedure.

The procedure tool 10 selected by the operator via the user interface (UI) may be operated by the vascular interventional procedure robot 230, which is driven by a remote control signal generated by the operator's manipulation of the operation rod 120, in the same motion as the motion of the operation rod 120 manipulated by the operator.

Referring again to FIG. 2, the vascular interventional procedure master device 100 according to an embodiment of the present disclosure may further include a control unit 170.

The control unit 170 may generate a remote control signal, which is to be provided to the slave device 200, based on physical quantities of the motion of the operation rod 120 measured by the first measurement unit 140 and the second measurement unit 150.

According to an embodiment of the present disclosure, various operation modes regarding the operation of the procedure tool 10 may be provided in the user interface (UI) so as to be selectable by the operator.

For example, a screw motion mode may be provided in the user interface (UI).

When the screw motion mode is selected by the operator, the control unit 170 may control the operation rod 120 such that the translational motion and the rotational motion of the operation rod 120 can be simultaneously performed when the operator manipulates the operation rod. Accordingly, the procedure tool 10 may also perform translational motion and rotational motion simultaneously by the remotely controlled vascular interventional procedure robot 230.

For example, when the procedure tool 10 passes through a thrombus, and when the screw motion mode is activated, the procedure tool 10 may easily pass through the thrombus.

Further, a leader and follower mode may be provided in the user interface (UI).

Figure 19:
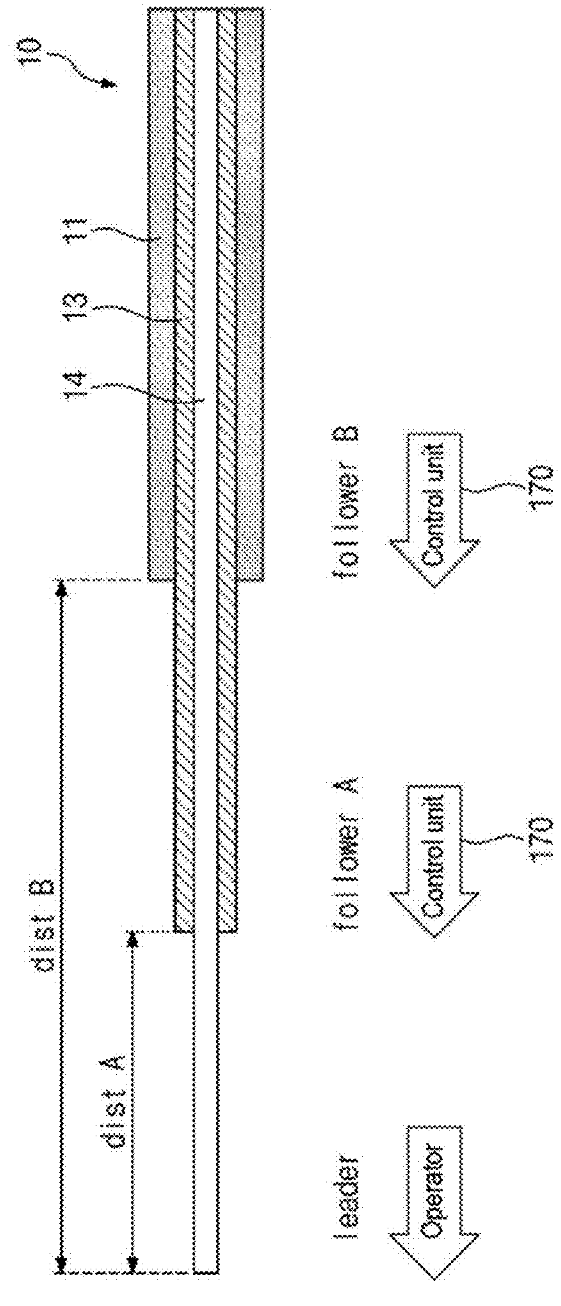
FIG. 19 illustrates a leader and follower mode operated by a control unit of a vascular interventional procedure master device according to an embodiment of the present disclosure.

Referring to FIG. 19, when the leader-and-follower mode is selected by the operator, the control unit 170 may configure, as a leader, any one procedure tool 10 controlled by a remote control signal generated based on the motion of the operation rod 120. For example, the control unit 170 may configure the micro guidewire 14, which is remotely controlled, as a leader.

Further, the control unit 170 may configure at least one other procedure tool 10, which is not remotely controlled, as a follower. For example, the control unit 170 may configure the microcatheter 13, which is not remotely controlled, as follower A, and configure the catheter 11 as follower B.

The control unit 170 may generate a remote control signal for operating a follower such that the follower follows the operation of a leader, and provide the signal to the slave device 200. For example, the control unit 170 may generate a remote control signal, which operates the microcatheter 13 configured as follower A and the catheter 11 configured as follower B, such that the microcatheter 13 and the catheter 11 follow the operation of the micro guidewire 14 configure as a leader, and may provide the signal to the slave device 200.

Accordingly, even when the operator does not remotely control the microcatheter 13 and the catheter, the microcatheter 13 and the catheter 11 may follow the operation of the remotely controlled micro guidewire 14. In this way, a predetermined distance (dist A) between the tip of the micro guidewire 14 configured as the leader and the tip of the microcatheter 13 configured as follower A, and a predetermined distance (dist B) between the tip of the micro guidewire 14 configured as the leader and the tip of the catheter 11 configured as follower B may be maintained.

In this case, even when the leader operates in the screw motion mode, the followers may perform only translational motion.

The leader and follower mode may be particularly effective on a straight path or a long path because multiple procedure tool 10 can be moved together.

Further, a tip sync motion mode may be provided in the user interface (UI).

Figure 20:
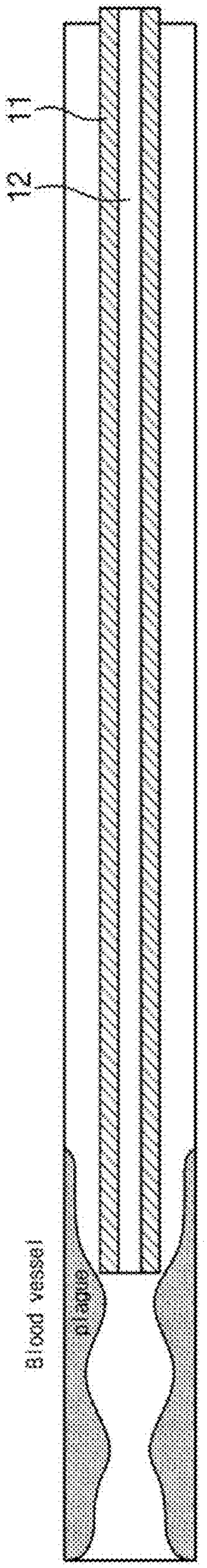
FIG. 20 illustrates a tip sync motion mode operated by a control unit of a vascular interventional procedure master device according to an embodiment of the present disclosure.

Referring to FIG. 20, when the leader and follower mode is selected and then the tip sync motion mode is further selected by the operator, the control unit 170 may generate a remote control signal for operating the follower such that the distance difference between the tip of the leader and the tip of the follower is zero, and may provide the signal to the slave device 200.

For example, the control unit 170 may generate a remote control signal for operating the catheter 11 such that the distance difference between the tip of the guidewire 12 configured as the leader and the tip of the catheter 11 configured as the follower is zero, and may provide the signal to the slave device 200.

When the device 10 operates in the tip sync motion mode, for example, the catheter 11 surrounds the circumference of the tip of the guidewire 12, thereby reinforcing the tip of the procedure tool 10 and enabling the tip of the procedure tool 10 to effectively pass through a vascular segment narrowed due to disease.

Further, a vibration mode may be provided in the user interface (UI).

Figure 21:
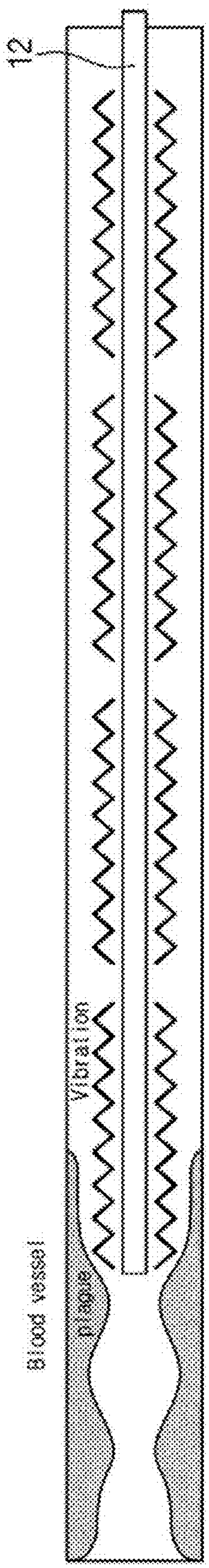
FIG. 21 illustrates a vibration mode operated by a control unit of a vascular interventional procedure master device according to an embodiment of the present disclosure.

Referring to FIG. 21, when the vibration mode is selected by the operator, the control unit 170 may generate a remote control signal for generating vibration and provide the signal to the slave device 200, so that vibration is applied to the procedure tool 10, for example, the guidewire 12, which is controlled based on a remote control signal generated based on the motion of the operation rod 120, while the guidewire 12 is being operated.

Accordingly, the forward, backward and rotational movements of the guidewire 12 may be smoothly performed. Thus, for example, when the guidewire 12 passes through a blood vessel narrowed due to disease, the guidewire 12 may more smoothly pass through the narrowed blood vessel by means of the generated vibration.

Figure 22:
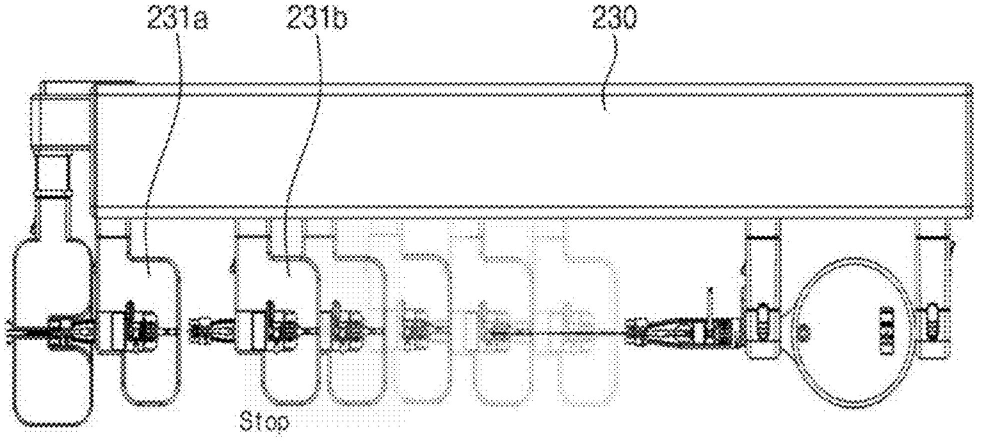
FIG. 22 illustrates controlling the operation of a module supporting a procedure tool by a control unit of a vascular interventional procedure master device according to an embodiment of the present disclosure.

Referring to FIG. 22, the control unit 170 may perform control to prevent a collision between multiple modules 231*a* and 231*b* which support respective procedure tool 10 in the vascular interventional procedure robot 230 of the slave device 200.

To this end, the control unit 170 may analyze a sensing value transmitted from a position sensor installed on each of the modules 231*a* and 231*b* supporting the respective procedure tool 10 such that the collision between the modules 231*a* and 231*b* is avoided when each of the modules 231*a* and 231*b* moves forward, moves backward, or stops. Based on the analyzed sensing value, the control unit 170 may generate a remote control signal for reconfiguring the movement operation of each of the multiple modules, and provide the signal to the slave device 200.

For example, when the module 231*b* supporting the guidewire 12 advances toward the module 231*a* supporting the catheter 11, and when it is determined that the module 231*a* supporting the catheter 11 will collide with the module 231*b* supporting the guidewire 12 if the module 231*b* continues to advance, the control unit 170 may generate a remote control signal for stopping the module 231*b* supporting the guidewire 12, and provide the signal to the slave device 200.

In this case, the control unit 170 may display an alarm regarding the reconfigured movement operation of each of the multiple modules 231*a* and 231*b* on the display unit 160 so as to be identified by the operator. For example, the control unit 170 may display, on the display unit 160, an alarm indicating that further advancement of the module 231*b* supporting the guidewire 12 is not possible.

Meanwhile, a back-and-return mode may be provided in the user interface (UI).

The back-and-return mode may be selected when injecting a drug through the procedure tool 10.

Figure 23:
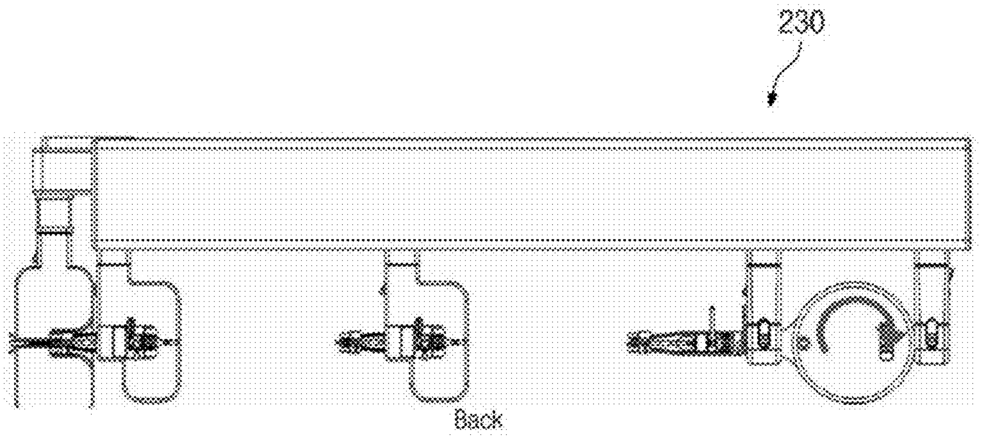
FIGS. 23 and 24 illustrate a back-and-return mode operated by a control unit of a vascular interventional procedure master device according to an embodiment of the present disclosure.

Referring to FIG. 23, when the back-and-return mode is selected by the operator, the control unit 170 may, in order to enable drug injection via one procedure tool 10, generate a remote control signal which retracts another procedure tool 10 inserted into the one procedure tool 10 such that the other instrument 10 is completely withdrawn from the inside to the outside of the one procedure tool 10, and provide the signal to the vascular interventional procedure robot 230 of the slave device 200.

Here, the one procedure tool 10 may be the catheter 11 or the microcatheter 13, and the other procedure tool 10 may be the guidewire 12 or the micro guidewire 14.

Figure 24:
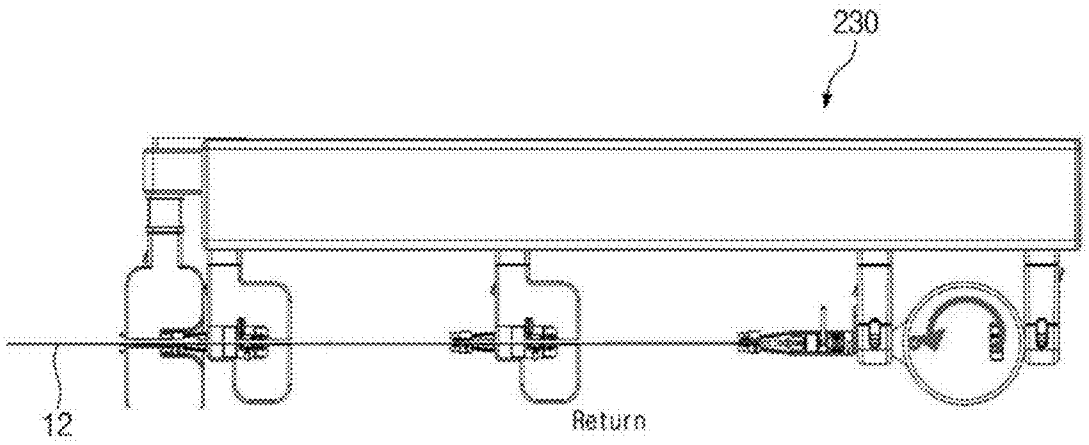

Subsequently, referring to FIG. 24, when the drug injection via the one procedure tool 10 is completed, the control unit 170 may generate a remote control signal for advancing the other instrument 10, for example, the guidewire 12, such that the guidewire 12 is inserted again to the original position inside the catheter 11, and provide the signal to the vascular interventional procedure robot 230 of the slave device 200.

In addition, the control unit 170 may generate an alarm recognizable to the operator whenever the procedure tool 10, which is controlled based on a remote control signal generated based on the motion of the operation rod 120 by the operator's manipulation, performs a translational motion of a predetermined distance.

Figure 25:
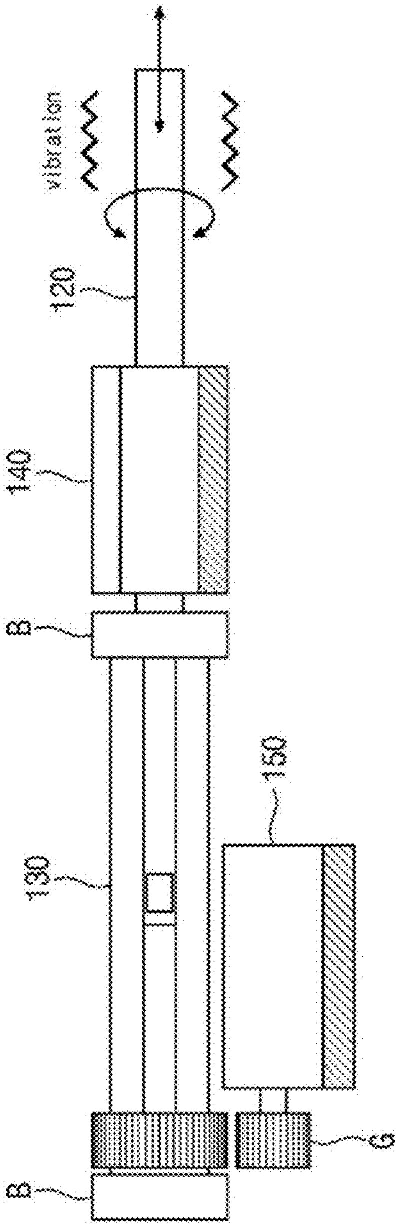
FIG. 25 illustrates a haptic mode operated by a control unit of a vascular interventional procedure master device according to an embodiment of the present disclosure.

Referring to FIG. 25, for example, when the procedure tool 10 moves a specific movement distance, for example, 1 mm, in response to the operator's manipulation of the operation rod 120, the control unit 170 may generate a vibration at the other longitudinal end of the operation rod 120 that is grasped by the operator so that the operator may recognize the movement of procedure tool 10. In this case, the control unit 170 may generate an alarm sound or the like in addition to the vibration.

Further, when a procedure tool 10 controlled by a remote control signal generated based on the motion of the operation rod 120 manipulated by the operator is operated, and when another procedure tool 10 interacting with the procedure tool 10 is unintentionally displaced by the procedure tool 10, the control unit 170 may generate a remote control signal for operating the other procedure tool 10 such that positional compensation is achieved to return the other procedure tool 10 to the original position, and provide the signal to the vascular interventional procedure robot 230 of the slave device 200.

Figure 26:
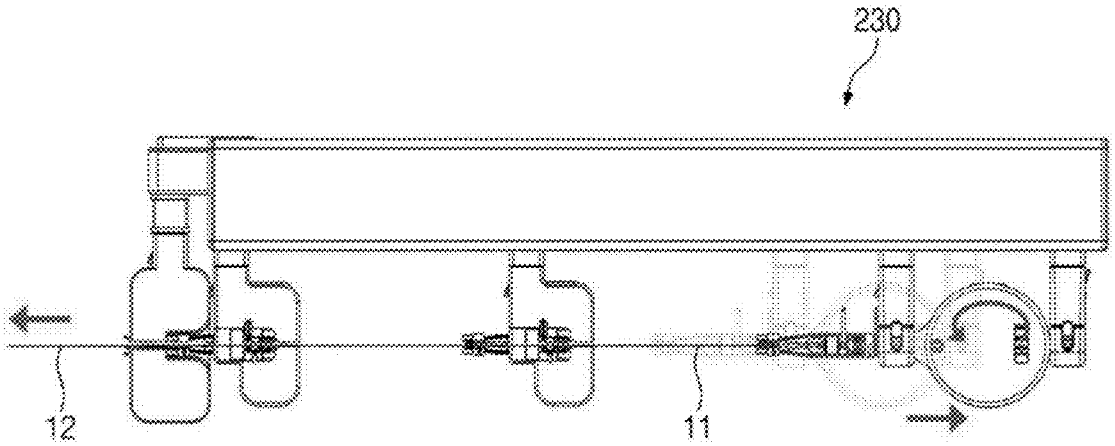
FIG. 26 illustrates a compensation operation performed by a control unit of a vascular interventional procedure master device according to an embodiment of the present disclosure.

Referring to FIG. 26, when the guidewire 12, which is controlled by a remote control signal generated based on the motion of the operation rod 120 by the operator's manipulation, advances, the catheter 11 longitudinally surrounding the guidewire 12 may advance a predetermined distance along the guidewire 12.

Accordingly, the control unit 170 may generate a remote control signal for returning the displaced catheter 11 to the original position, and provide the signal to the vascular interventional procedure robot 230 of the slave device 200.

Accordingly, a procedure tool 10, which is not remotely controlled by the operator, may maintain a fixed position within the human body.

Meanwhile, an anti-stent jumping motion mode may be provided in the user interface (UI).

When the anti-stent jumping motion mode is selected by the operator, the control unit 170 may, before placing a stent in a blood vessel, generate a remote control signal for retracting the stent such that when the procedure tool 10, which is controlled based on a remote control signal generated based on the motion of the operation rod 120, is retracted, the stent is also retracted, in order to reduce a repulsive force between a blood vessel wall and the procedure tool 10, thereby preventing the stent from jumping, and may and provide the signal to the slave device 200. Here, the distance by which the stent is retracted may be shorter than the distance by which the procedure tool 10 is retracted.

In the anti-stent jumping motion mode, the control unit 170 may generate a remote control signal to position the stent within the blood vessel while completely retracting the procedure tool 10, e.g., the microcatheter 13, when the procedure tool 10 and the stent are retracted to a distance at which the repulsive force between the blood vessel wall and the procedure tool 10 is reduced to some extent.

Further, the control unit 170 may automatically return the operation rod 120 to the initial position when a stroke higher than a predetermined stroke is applied to the operation rod 120 for translational motion and rotational motion of the operation rod 120.

Figure 27:
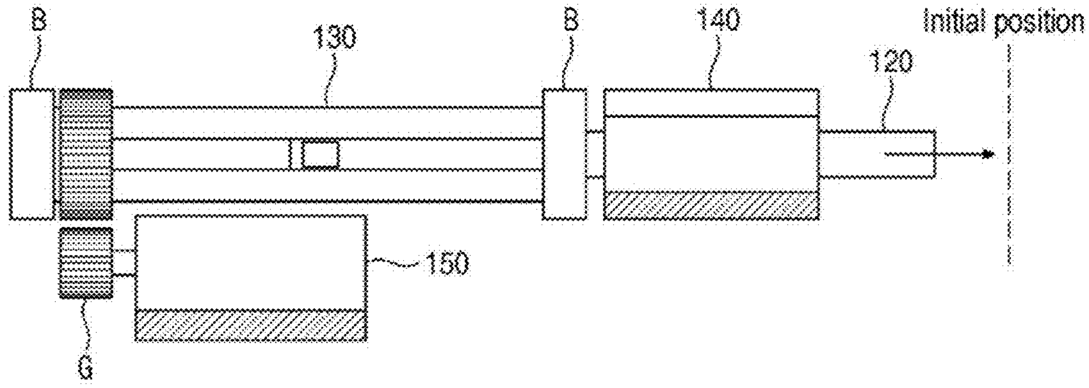
FIGS. 27 and 28 illustrate an automatic return operation of an operation rod performed by a control unit of a vascular interventional procedure master device according to an embodiment of the present disclosure.

Referring to FIG. 27, if a stroke higher than a predetermined stroke is applied by the operator when advancing the operation rod 120, the control unit 170 may control the operation rod 120 to automatically return to the initial position. Accordingly, the operation rod 120 may be automatically retracted when the operator stops manipulation.

Figure 28:
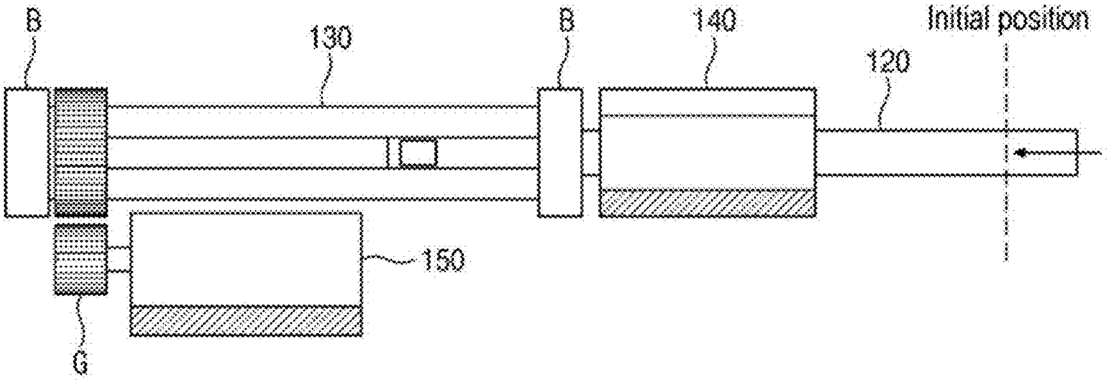

Also, referring to FIG. 28, if a stroke higher than a predetermined stroke is applied by the operator when retracting the operation rod 120, the control unit 170 may control the operation rod 120 to automatically return to the initial position. Accordingly, the operation rod 120 may be automatically advanced when the operator stops manipulation.

As a result, when the operator manipulates the operation rod 120, repetitive insertion/retraction/rotation/screwing motions may be easily accomplished.

According to an embodiment of the present disclosure, the user interface (UI) may be provided with various operation modes for the procedure tool 10 in addition to the aforementioned operation modes. For example, the operator may select, from the user interface (UI), various modes of movement of the procedure tool 10, e.g., constant speed, slow speed, acceleration, deceleration, simultaneous rotation and insertion, simultaneous rotation and retraction, vibration, and the like, so that such precise motion control may be reflected in the procedure tool 10 when manipulating the operation rod 120.

Through such precise motion control, the procedure tool 10 may be moved slowly, for example, in the case of stent retrieval, stent placement, and coil placement, thereby enabling more accurate placement of the procedure tool 10.

Further, when the operator manipulates the operation rod 120 to continuously move the procedure tool 10 through the vascular interventional procedure robot 230, the control unit 170 may control the vascular interventional procedure robot 230 such that when the motion of the operation rod 120 manipulated by the operator satisfies a specific condition, the insertion, retraction, and rotation of the procedure tool 10 may be performed continuously or intermittently even without further manipulation of the operation rod 120.

The user interface (UI) may further be provided with a free mode and a loading mode.

When the free mode is selected by the operator, the control unit 170 may cut off power applied to a driving motor of the vascular interventional procedure robot 230 to allow the operator to freely move the procedure tool 10 while holding the procedure tool 10.

Further, when the loading mode is selected by the operator, the control unit 170 may apply power to the driving motor of the vascular interventional procedure robot 230 such that the procedure tool 10 is operated only when the operation rod 120 is manipulated.

When one step of the procedure is completed, the operator may replace the procedure tool and mount a different procedure tool 10 on the vascular interventional procedure robot 230 to perform a subsequent step of the procedure.

In this case, the control unit 170 may control the vascular interventional procedure robot 230 to reposition the module supporting the procedure tool 10. Thus, the operator may easily replace the procedure tool 10.

According to an embodiment of the present disclosure, the user interface (UI) may be provided with an additional procedure step, in addition to the above-described operation modes.

Accordingly, in the user interface (UI), the operator may select a procedure step to be performed. In this way, when a procedure step is selected, the user interface (UI) may display a procedure tool selection button according to the selected procedure step. In this case, a procedure tool selection button which is not used for the selected procedure step may be disabled or not displayed.

Although not illustrated, the vascular interventional procedure master device 100 according to an embodiment of the present disclosure may further include a storage.

The storage may store information such as the movement of the operation rod 120 according to the manipulation of the operator, the corresponding movement of the vascular interventional procedure robot 230, sensor values, and the like in order of time, action, event occurrence, and the like while performing a procedure step.

The vascular interventional procedure master device 100 according to an embodiment of the present disclosure may be used while attached to a cockpit or detached from the cockpit.

Meanwhile, in a procedure step that requires the simultaneous use of two or more procedure tool 10, the vascular interventional procedure master device 100 according to an embodiment of the present disclosure may be provided in a dual mode.

Accordingly, the operator may simultaneously manipulate the operation rods 120 of both vascular interventional procedure master devices 100 with both hands. At this time, the alignment angle of both vascular interventional procedure master devices 100 may be changed so that the operator can easily grasp the operation rod 120 with both hands.

In the dual mode in which two vascular interventional procedure master devices 100 are provided, the operator may designate a procedure tool 10 which is operated by each of the operation rods 120 of both vascular interventional procedure master devices 100. Accordingly, the two procedure tool 10 may move simultaneously, but independently, in response to the operator's manipulation of the two operation rods 120.

As described above, the vascular interventional procedure master device 100 according to an embodiment of the present disclosure may precisely and remotely control the operation of the procedure tool 10 through various operation modes, thereby enabling smooth insertion of the procedure tool 10 up to the target branch. Accordingly, the efficiency of the vascular interventional procedure may be improved.

Although the present disclosure has been described in detail using embodiments, the scope of the present disclosure is not limited to any specific embodiment and should be construed in accordance with the scope of the appended patent claims. Furthermore, those skilled in the art will understand that numerous modifications and variations can be made without departing from the scope of the present disclosure.

What is claimed is:

1. A method performed by a master device for remotely controlling a vascular interventional procedure robot, the method comprising:

(a) generating a first remote advancement control signal for causing at least one guide device to reach a target branch in response to a user's first advancement operation of at least one operation rod configured to perform translational and rotational motions, and providing the first remote advancement control signal to the vascular interventional procedure robot;

(b) generating a second remote advancement control signal for causing at least one catheter to reach the target branch by following the at least one guide device in response to the user's second advancement operation of the at least one operation rod, and providing the second remote advancement control signal to the vascular interventional procedure robot;

(c) generating a first remote retraction control signal for removing the at least one guide device from the at least one catheter by withdrawing the at least one guide device in a direction opposite to that of insertion in response to the user's first retraction manipulation of the at least one operation rod, and providing the first remote retraction control signal to the vascular interventional procedure robot; and (d) generating a third remote advancement control signal for causing at least one procedure device to reach the target branch by following the at least one catheter in response to the user's third advancement operation of the at least one operation rod, and providing the third remote advancement control signal to the vascular interventional procedure robot;

wherein the at least one operation rod comprises two operation rods, wherein the two operation rods are manipulated to control at least two instruments among the at least one guide device, the at least one catheter and the at least one procedure device to move simultaneously but independently, thereby generating two corresponding remote control signals based on independent manipulations of the two operation rods, respectively, and wherein the two corresponding remote control signals are generated based on motion scaling values adjusted independently for each of the two operation rods, each of the motion scaling values indicating a ratio of a range of movement of a corresponding instrument among the at least two instruments to a range of movement of a corresponding operation rod among the two operation rods.

2. The method of claim 1, further comprising displaying, on a display of the master device, a procedure interface for selecting a procedure step and a procedure tool driven by the vascular interventional procedure robot.

3. The method of claim 2, wherein:

step (a) comprises:

acquiring a first user input for selecting a first interface corresponding to the at least one guide device included in the procedure interface; and generating, based on the first user input, a signal requesting the at least one guide device to be mounted to the vascular interventional procedure robot, and transmitting the signal to the vascular interventional procedure robot;

step (b) comprises:

acquiring a second user input for selecting a second interface corresponding to the at least one catheter included in the procedure interface; and generating, based on the second user input, a signal requesting the at least one catheter to be mounted to the vascular interventional procedure robot, and transmitting the signal to the vascular interventional procedure robot; and step (d) comprises:

acquiring a third user input for selecting a third interface corresponding to the at least one procedure device included in the procedure interface; and generating, based on the third user input, a signal requesting the at least one procedure device to be mounted to the vascular interventional procedure robot, and transmitting the signal to the vascular interventional procedure robot.

4. The method of claim 2, wherein the procedure interface further comprises a tip sync motion mode and a screw motion mode, and the method further comprises:

when the tip sync motion mode is selected by a fourth user input, generating a remote control signal for operating at least one procedure tool such that a distance between a tip of one procedure tool and a tip of another procedure tool becomes zero, and providing the remote control signal to the vascular interventional procedure robot, and when the screw motion mode is selected by a fifth user input, generating a remote control signal that causes a translational motion and a rotational motion of the procedure tool to be simultaneously performed in response to the user's manipulation of the at least one of the two operation rods, and providing the remote control signal to the vascular interventional procedure robot.

5. The method of claim 2, wherein the procedure interface further comprises a back-and-return mode, and the method further comprises:

in case of injecting a medical material through the procedure tool, selecting the back-and-return mode included in the procedure interface; and when the back-and-return mode is selected by a user input, generating a remote control signal for: retracting another procedure tool inserted into the procedure tool such that the other procedure tool is withdrawn from the inside to the outside of the procedure tool; and when the injection of the medical material via the procedure tool is completed, advancing the other procedure tool such that the other procedure tool is reinserted into the procedure tool.

6. The method of claim 2, wherein the procedure interface further comprises:

a communication connection button for establishing wireless communication with the vascular interventional procedure robot;

a communication disconnection button for disconnecting wireless communication with the vascular interventional procedure robot; and an emergency stop button for stopping operation of the procedure tool of the vascular interventional procedure robot.

7. The method of claim 2, wherein the procedure interface further comprises:

a free mode button for cutting off power applied to a driving motor of the vascular interventional procedure robot such that a procedure tool of the vascular interventional procedure robot is operated only manually by the user; and a loading mode button for applying power to the driving motor of the vascular interventional procedure robot such that the procedure tool of the vascular interventional procedure robot is operated only when the at least one of the two operation rods is manipulated.

8. The method of claim 2, wherein the procedure interface further comprises multiple scaling buttons, and wherein the motion scaling values are adjusted independently for each of the two operation rods via the multiple scaling buttons.

9. The method of claim 2, wherein the procedure interface further comprises a leader and follower mode, and the method further comprises, when the leader and follower mode is selected by a user input, configuring a first procedure tool, which is controlled based on a remote control signal, as a leader, configuring a second procedure tool, which is not controlled based on the remote control signal, as a follower, generating a remote control signal that operates the second procedure tool to follow the movement of the first procedure tool based on the user's manipulation of the at least one of the two operation rods, and providing the remote control signal to the vascular interventional procedure robot.

10. The method of claim 2, wherein the procedure interface further comprises a vibration mode, and the method further comprises, when the vibration mode is selected by a user input, generating a remote control signal that generates a vibration such that the vibration is applied to a procedure tool, which is controlled based on a remote control signal generated based on a motion of the at least one of the two operation rods, during operation of the procedure tool, and providing the remote control signal to the vascular interventional procedure robot.

11. The method of claim 2, wherein the procedure interface comprises an anti-stent jumping motion mode, and the method comprises, in case that the anti-stent jumping mode is selected by a user input, generating, before placing a stent in a blood vessel, a remote control signal for retracting the stent such that when a procedure tool, which is controlled based on a remote control signal generated based on the motion of the at least one of the two operation rods, is retracted, the stent is also retracted, and providing the remote control signal to the vascular interventional procedure robot, wherein a distance by which the stent is retracted is shorter than a distance by which the procedure tool is retracted.

12. The method of claim 1, wherein the first advancement operation comprises an operation to advance the at least one of the two operation rods while rotating; and the at least one guide device is inserted toward the target branch while being rotated by the vascular interventional procedure robot in response to the first remote advancement control signal.

13. The method of claim 1, wherein step (a) comprises generating the first remote advancement control signal, based on a first physical quantity, measured by a first measuring unit and related to a translational motion of the at least one of the two operation rods by the first advancement operation, and a second physical quantity, measured by a second measuring unit and related to a rotational motion of the at least one of the two operation rods by the first advancement operation.

14. The method of claim 1, wherein, in steps (a) and (b), the at least one guide device and the at least one catheter are introduced into a first target branch, and in step (d), the at least one procedure device is introduced into a second target branch branched from the first target branch.

15. The method of claim 1, comprising:

after step (c) and before step (d), (e) generating a fourth remote advancement control signal for causing a micro guidewire inserted into the at least one procedure device to reach the target branch in response to the user's fourth advancement operation of the at least one of the two operation rods, and providing the fourth remote advancement control signal to the vascular interventional procedure robot.

16. The method of claim 15, wherein, in step (d), the at least one procedure device reaches the target branch by following the micro guidewire.

17. The method of claim 15, wherein, in steps (a) and (b), the at least one guide device and the at least one catheter are introduced into a first target branch, in step (e), the micro guidewire is introduced into a second target branch branched from the first target branch, and in step (d), the at least one procedure device is introduced into the second target branch along the micro guidewire.

18. The method of claim 15, further comprising:

after step (d), (f) generating a second remote retraction control signal for removing the micro guidewire from the at least one procedure device while withdrawing the micro guidewire in a direction opposite to that of insertion in response to the user's second retraction manipulation of the at least one of the two operation rods, and providing the second remote retraction control signal to the vascular interventional procedure robot.

19. The method of claim 1, further comprising, after step (d), at least one of:

(g) generating a first signal for suctioning a thrombus from the target branch through the at least one procedure device, and providing the first signal to the vascular interventional procedure robot;

(h) generating a second signal for performing aneurysm coil embolization through the at least one procedure device, and providing the second signal to the vascular interventional procedure robot;

(i) generating a third signal for performing angiography through the at least one procedure device, and providing the third signal to the vascular interventional procedure robot; or (j) generating a fourth signal for injecting at least one of a contrast agent, a drug, or an embolic material into the target branch through the at least one procedure device, and providing the fourth signal to the vascular interventional procedure robot.

20. The method of claim 1, further comprising after step (d), (k) generating a fifth remote advancement control signal for causing a medical device to reach the target branch by following the at least one procedure device in response to the user's fifth advancement operation of the at least one of the two operation rods, and providing the fifth remote advancement control signal to the vascular interventional procedure robot.

21. The method of claim 20, wherein step (k) comprises:

acquiring a user input for selecting a fifth interface corresponding to the medical device included in the procedure interface; and generating, based on the user input, a signal requesting the medical device to be mounted to the vascular interventional procedure robot in place of the procedure tool, and transmitting the signal to the vascular interventional procedure robot.

22. The method of claim 1, wherein in step (b), a position of a distal end of the at least one catheter is maintained within the target branch; and in step (d), the position of the distal end of the at least one catheter and a position of a distal end of the at least one procedure device are maintained within the target branch.

23. The method of claim 1, further comprising when a surgical procedure corresponding to each operation is completed, generating a remote control signal for repositioning a module supporting a procedure tool controlled by the vascular interventional procedure robot to perform a surgical procedure for a subsequent operation, and providing the remote control signal to the vascular interventional procedure robot.

24. The method of claim 1, further comprising in case that a stroke higher than a predetermined stroke is applied to the at least one of the two operation rods when the user advances or retracts the at least one of the two operation rods, returning the at least one of the two operation rods to an initial position before being manipulated by the user.

25. The method of claim 1, further comprising:

analyzing a sensing value transmitted from a position sensor installed in each of multiple modules supporting respective procedure tools in the vascular interventional procedure robot such that collisions between the multiple modules are avoided in case that each of multiple modules advances, retracts, or stops;

generating a remote control signal for reconfiguring a movement operation of each of the multiple modules, based on the analyzed sensing value, and providing the remote control signal to the vascular interventional procedure robot; and displaying, on a display, an alarm for the reconfigured movement operation of each of the multiple modules.

26. The method of claim 1, further comprising generating a vibration at the other longitudinal end of the at least one of the two operation rods or generating an alarm recognizable to the user, whenever a procedure tool controlled based on a remote control signal generated in response to the user's manipulation of the at least one of the two operation rods translates a predetermined distance.

27. The method of claim 1, further comprising when a third procedure tool, which is controlled based on a remote control signal generated based on the motion of the at least one of the two operation rods by the user's manipulation, is operated, and a position of a fourth procedure tool interacting with the third procedure tool is moved by the operation of the third procedure tool, generating a remote control signal for operating the fourth procedure tool such that position compensation is performed to return the fourth procedure tool to an original position before being moved by the operation of the third procedure tool, and providing the remote control signal to the vascular interventional procedure robot.

28. A master device comprising:

one or more processors; and one or more memories configured to store instructions to be executed by the one or more processors, wherein, the one or more processors are configured to, when the instructions are executed, (a) generate a first remote advancement control signal for causing at least one guide device to reach a target branch in response to a user's first advancement operation of at least one operation rod configured to perform translational and rotational motions, and provide the first remote advancement control signal to vascular interventional procedure robot;

(b) generate a second remote advancement control signal for causing at least one catheter to reach the target branch by following the at least one guide device in response to the user's second advancement operation of the at least one operation rod, and provide the second remote advancement control signal to the vascular interventional procedure robot;

(c) generate a first remote retraction control signal for removing the at least one guide device from the at least one catheter by withdrawing the at least one guide device in a direction opposite to that of insertion in response to the user's first retraction manipulation of the at least one operation rod, and provide the first remote retraction control signal to the vascular interventional procedure robot; and (d) generate a third remote advancement control signal for causing at least one procedure device to reach the target branch by following the at least one catheter in response to the user's third advancement operation of the at least one operation rod, and provide the third remote advancement control signal to the vascular interventional procedure robot;

wherein the at least one operation rod comprises two operation rods, and wherein the one or more processors are further configured to:

generate two corresponding remote control signals based on independent manipulations of the two operation rods, respectively, such that at least two instruments among the at least one guide device, the at least one catheter, and the at least one procedure device move simultaneously but independently; and generate the two corresponding remote control signals based on motion scaling values adjusted independently for each of the two operation rods, each of the motion scaling values indicating a ratio of a range of movement of a corresponding instrument among the at least two instruments to a range of movement of a corresponding operation rod among the two operation rods.

29. A method performed by a master device for remotely controlling a vascular interventional procedure robot configured to drive a procedure tool, the method comprising:

(a) generating a first remote advancement control signal for causing at least one guide device to reach a target branch in response to a user's first advancement operation of at least one operation rod configured to perform translational and rotational motions, and providing the first remote advancement control signal to the vascular interventional procedure robot;

(b) generating a second remote advancement control signal for causing at least one catheter to reach the target branch by following the at least one guide device in response to the user's second advancement operation of the at least one operation rod, and providing the second remote advancement control signal to the vascular interventional procedure robot; and (l) injecting a diagnostic agent into the target branch through the at least one catheter, wherein after step (b) and before step (l), (c) generating a first remote retraction control signal for removing the at least one guide device from the at least one catheter by withdrawing the at least one guide device in a direction opposite to that of insertion in response to the user's first retraction manipulation of the at least one operation rod, and providing the first remote retraction control signal to the vascular interventional procedure robot.

* * * * *